United States Patent
Kim et al.

(10) Patent No.: US 9,535,044 B2
(45) Date of Patent: Jan. 3, 2017

(54) APPARATUS AND METHOD FOR MEASURING AGING ENVIRONMENT

(71) Applicants: ELECTRONICS AND TELECOMMUNICATIONS RESEARCH INSTITUTE, Daejeon (KR); DONGAONE CO., LTD., Seoul (KR)

(72) Inventors: Bong Wan Kim, Daejeon (KR); Jun Wook Lee, Chungcheongbuk-do (KR); Hyun-joong Kang, Gyeongsangnam-do (KR); Sungsoo Kang, Daejeon (KR); Jong-Suk Chae, Daejeon (KR)

(73) Assignees: ELECTRONICS AND TELECOMMUNICATIONS RESEARCH INSTITUTE, Daejeon (KR); DONGAONE CO., LTD., Seoul (KR)

(*) Notice: Subject to any disclaimer, the term of this patent is extended or adjusted under 35 U.S.C. 154(b) by 637 days.

(21) Appl. No.: 14/027,537

(22) Filed: Sep. 16, 2013

(65) Prior Publication Data

US 2014/0081580 A1     Mar. 20, 2014

(30) Foreign Application Priority Data

Sep. 17, 2012 (KR) .................. 10-2012-0103037

(51) Int. Cl.
| | | |
|---|---|---|
| G01N 33/04 | (2006.01) |
| G01N 33/00 | (2006.01) |
| G01N 33/14 | (2006.01) |
| C12G 3/07 | (2006.01) |
| C12H 1/22 | (2006.01) |
| C12C 11/00 | (2006.01) |
| C12G 1/00 | (2006.01) |

(52) U.S. Cl.
CPC ........ *G01N 33/0004* (2013.01); *G01N 33/146* (2013.01); *C12C 11/003* (2013.01); *C12G 1/00* (2013.01); *C12G 3/065* (2013.01); *C12H 1/22* (2013.01)

(58) Field of Classification Search
CPC .. G01N 33/0004; G01N 33/146; C12G 3/065; C12G 1/00; C12H 1/22
See application file for complete search history.

(56) References Cited

U.S. PATENT DOCUMENTS

| | | | | |
|---|---|---|---|---|
| 2002/0030585 A1* | 3/2002 | Doi | ...... | A61B 5/0028 340/5.64 |
| 2002/0168446 A1* | 11/2002 | Zimlich, III | ...... | C12G 3/005 426/11 |
| 2003/0219062 A1 | 11/2003 | Egidio | | |
| 2008/0000356 A1* | 1/2008 | Eustis | ...... | C12H 1/16 99/277.2 |
| 2009/0136885 A1 | 5/2009 | Manno | | |

(Continued)

FOREIGN PATENT DOCUMENTS

KR     1020090046299 A     5/2009

*Primary Examiner* — John Breene
*Assistant Examiner* — Mohammad Islam
(74) *Attorney, Agent, or Firm* — Ladas & Parry LLP

(57) ABSTRACT

An aging environment measurement apparatus measures aging environment data within an oak barrel and transmits the measured aging environment data within the oak barrel to a server, and the aging environment measurement apparatus is mounted in a bung of the oak barrel.

14 Claims, 8 Drawing Sheets

(56) References Cited

U.S. PATENT DOCUMENTS

| | | | | |
|---|---|---|---|---|
| 2009/0188588 A1* | 7/2009 | Whiting | ............ | B27H 5/08 |
| | | | | 147/1 |
| 2011/0101010 A1* | 5/2011 | Maiocco | ............ | B65D 81/245 |
| | | | | 220/720 |
| 2011/0217205 A1 | 9/2011 | Peeters | | |
| 2012/0204728 A1* | 8/2012 | Roleder | ............ | C12G 3/065 |
| | | | | 99/277.2 |
| 2013/0045300 A1* | 2/2013 | Robillard | ............ | C12G 3/065 |
| | | | | 426/11 |
| 2013/0317764 A1* | 11/2013 | Kumar | ............ | G01F 23/296 |
| | | | | 702/51 |

\* cited by examiner

APPARATUS AND METHOD FOR MEASURING AGING ENVIRONMENT

CROSS-REFERENCE TO RELATED APPLICATION

This application claims priority to and the benefit of Korean Patent Application No. 10-2012-0103037 filed in the Korean Intellectual Property Office on Sep. 17, 2012, the entire contents of which are incorporated herein by reference.

BACKGROUND OF THE INVENTION (a) Field of the Invention

The present invention relates to a method and apparatus for measuring an aging environment. More particularly, the present invention relates to a method and apparatus for measuring an environment of a winery, which is a wine brewery.

(b) Description of the Related Art

In general, a winery environment measurement apparatus measures an environment state such as ambient temperature and humidity of an aging apparatus using a sensor that is installed within a winery.

Further, when measuring internal temperature of the aging apparatus, a winery manager removes a bung of the aging apparatus, inserts a temperature sensor into the bung hole, measures the internal temperature of the aging apparatus, and writes the measured temperature by hand. Therefore, it is inconvenient to measure an internal temperature of the aging apparatus, and an error may occur due to erroneous writing of the winery manager.

In order to improve such a problem, a method of automatically measuring the internal temperature of the aging apparatus by attaching a sensor to each aging apparatus was suggested.

First aging of wine is performed on a large scale in a large aging apparatus that is made of various materials such as cement, stainless, and wood. Such a first aging apparatus is fixed to the winery and is managed by the winery, and thus by attaching a sensor to the first aging apparatus, environment information can be continuously collected.

Secondary aging of the wine is performed in an oak barrel that is smaller than the aging apparatus for first aging of wine. First aging is performed for a few weeks, but secondary aging is generally performed over a long term for 18 months or more. Oak barrels, which are a secondary aging apparatus, are necessary in a larger number than that containers of the first aging apparatus and are a consumption apparatus, not an apparatus that is fixed to the winery, and a large amount of secondary aging apparatuses are newly bought every year and are installed in the winery.

When producing high-quality wine, in order to maintain high quality, an oak barrel is generally used only once time, and even in a winery that produces intermediate grade wine, an oak barrel is used only for a limited number of times. Due to such a reason, because a method of attaching a sensor to the oak barrel has low economic efficiency, a method of attaching a sensor to the secondary aging apparatus is not appropriate.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a method and apparatus for measuring an aging environment having advantages of effectively measuring an aging environment of an oak barrel with a low cost.

An exemplary embodiment of the present invention provides an aging environment measurement apparatus that measures an aging environment within an oak barrel that contains liquor. The aging environment measurement apparatus includes a measurement sensing unit and a controller. The measurement sensing unit measures aging environment data within the oak barrel. The controller collects the aging environment data and transmits the collected aging environment data to a server. The aging environment measurement apparatus is mounted in a bung of the oak barrel.

The aging environment measurement apparatus may further include a start detection unit that generates a start signal according to detection of an aging environment measurement start. The controller may supply power to the measurement sensing unit according to the start signal.

The controller may enter a sleep mode when transmission of the aging environment data is complete, and may awake from the sleep mode according to the start signal.

The controller may intercept power from being supplied to the measurement sensing unit before entering the sleep mode.

The start detection unit may include at least one of a push switch that detects pressing of the bung from the outside and that generates the start signal, a touch sensor that senses touch of the bung from the outside and that generates the start signal, and a vibration sensor that senses a vibration of the bung and that generates the start signal.

The controller may supply power to the measurement sensing unit according to an aging environment measurement cycle.

The controller may enter a sleep mode when transmission of the aging environment data is complete, and awake from the sleep mode according to the aging environment measurement cycle.

The bung may include an outer edge frame that encloses to form an empty space, and the aging environment measurement apparatus may be mounted in the empty space.

Another embodiment of the present invention provides a method in which an aging environment measurement apparatus measures an aging environment within an oak barrel that contains liquor. The method includes measuring aging environment data within the oak barrel, and transmitting the aging environment data within the oak barrel to a server. The aging environment measurement apparatus may be mounted in a bung of the oak barrel. The measuring of aging environment data may include detecting an aging environment measurement start according to detection of the aging environment measurement start, and supplying power to a measurement sensing unit that measures the aging environment data. The transmitting of the aging environment data may include processing and storing the aging environment data, and intercepting power from being supplied to the measurement sensing unit when processing and storage of the aging environment data are complete.

The measuring of aging environment data may include supplying power to the measurement sensing unit that measures the aging environment data according to an aging environment measurement cycle, and the transmitting of the aging environment data may include processing and storing the aging environment data and intercepting power from being supplied to the measurement sensing unit when processing and storage of the aging environment data are complete.

The transmitting of the aging environment data may include intercepting the power supply and setting a time to awake, and entering a sleep mode according to the aging environment measurement cycle.

DETAILED DESCRIPTION OF THE EMBODIMENTS

Figure 1:
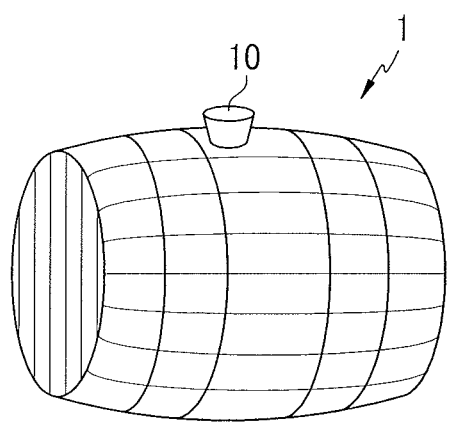
FIG. 1 is a diagram illustrating an example of an oak barrel according to an exemplary embodiment of the present invention.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In addition, in the specification and claims, unless explicitly described to the contrary, the word "comprise" and variations such as "comprises" or "comprising" will be understood to imply the inclusion of stated elements but not the exclusion of any other elements.

Hereinafter, a method and apparatus for measuring an aging environment according to an exemplary embodiment of the present invention will be described in detail with reference to the drawings.

FIG. 1 is a diagram illustrating an example of an oak barrel according to an exemplary embodiment of the present invention.

Referring to FIG. 1, an oak barrel 1 is made of oak as a major material, and is manufactured by connecting wooden oak boards using steel hoops.

The oak barrel 1 is manufactured in a dense structure to prevent wine from leaking through a gap between wooden staves while aging, a hole for injecting and managing wine is formed at the center of the oak barrel 1, and by blocking the hole with a bung 10, wine is prevented from contacting the air.

The bung 10 is made of silicon or rubber, prevents wine from leaking, and intercepts air flow.

The oak barrel 1 has various sizes from 1 gallon (about 3.79 liters) to 60 gallons (about 227 liters) based on a capacity for aging wine.

The oak barrel 1 is generally distributed with a method of using a new oak barrel one time in a winery that produces high-quality wine, selling the used oak barrel to be used in a winery that produces middle and low price wine, using the used oak barrel several times in the middle and low price wine winery, and then selling the used oak barrel to a whisky production company. Therefore, it is difficult for the winery to attach an aging environment measurement apparatus having a rising unit cost to the oak barrel 1 that is used as a consumption good.

In order to overcome such a problem, in an exemplary embodiment of the present invention, the bung 10 of the oak barrel 1 is used for measurement of an aging environment instead of the oak barrel 1.

Figure 2:
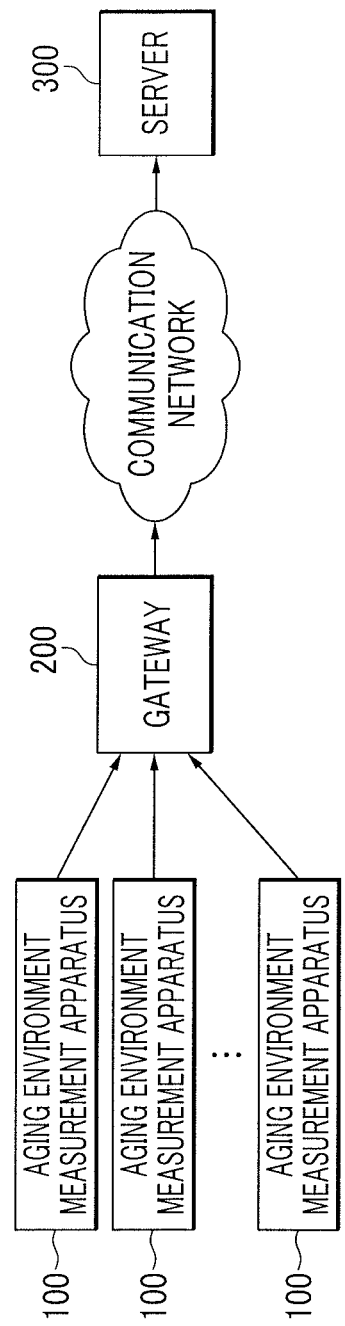
FIG. 2 is a diagram illustrating an aging environment monitoring system according to an exemplary embodiment of the present invention.

FIG. 2 is a diagram illustrating an aging environment monitoring system according to an exemplary embodiment of the present invention.

Referring to FIG. 2, the aging environment monitoring system includes an aging environment measurement apparatus 100, a gateway 200, and a server 300.

The aging environment measurement apparatus 100 is mounted in the bung 10 of the oak barrel 1, measures aging environment data, and transfers the measured aging environment data to the gateway 200. The aging environment measurement apparatus 100 may transfer aging environment data to the gateway 200 through a low power communication method such as IEEE 802.15.4.

The aging environment data may include temperature, acidity (pH), tartaric acid (TA), volatile acidity (VA), and carbon dioxide ($CO_2$) according to a kind of liquor while aging.

The gateway 200 receives aging environment data from the aging environment measurement apparatus 100, collects aging environment data of the oak barrel, and transfers the collected aging environment data of the oak barrel to the server 300 through a communication network.

The server 300 manages aging environment data of the oak barrel 1, and the aging environment data of the oak barrel 1 is analyzed by a winery wine manufacturer.

Figure 3:
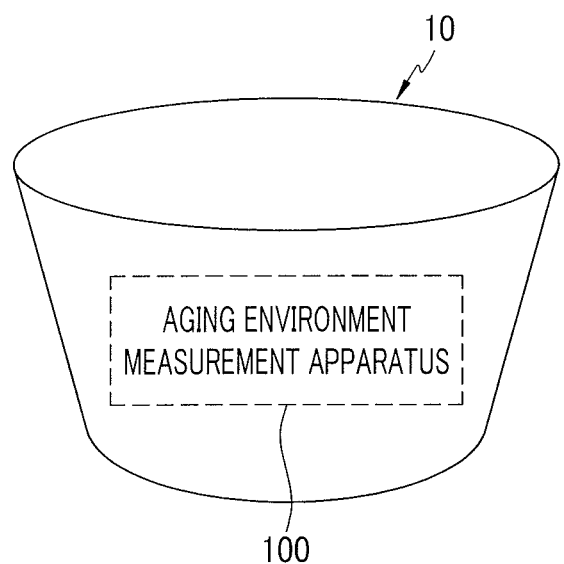
FIG. 3 is a diagram illustrating an example in which an aging environment measurement apparatus is mounted in a bung according to an exemplary embodiment of the present invention.

FIG. 3 is a diagram illustrating an example in which an aging environment measurement apparatus is mounted in a bung according to an exemplary embodiment of the present invention.

As shown in FIG. 3, the aging environment measurement apparatus 100 is mounted in the bung 10 of the oak barrel 1. The bung 10 is necessary for all oak barrels 1, and the aging environment measurement apparatus 100 is installed at an internal space of the bung 10.

Even if a new oak barrel is used in the winery, such a bung 10 may be used for the new oak barrel. Because the bung 10 can be recycled, the aging environment measurement apparatus 100 is installed in the bung 10. That is, when the aging environment measurement apparatus 100 is mounted in the bung 10, the aging environment measurement apparatus 100 can be continuously used for wine management and aging environment information acquisition of wine, and thus economic loss can be reduced compared with when installing the aging environment measurement apparatus 100 in the oak barrel 1.

Figure 4:
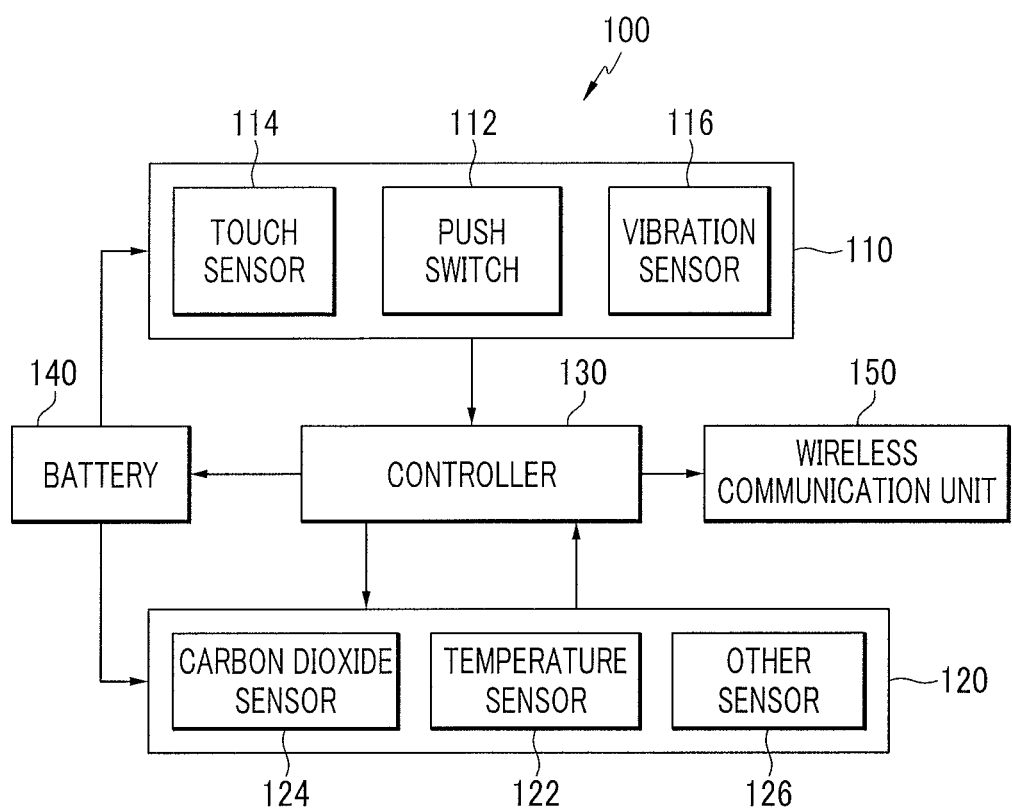
FIG. 4 is a block diagram illustrating a configuration of an aging environment measurement apparatus according to an exemplary embodiment of the present invention.
Figure 5:
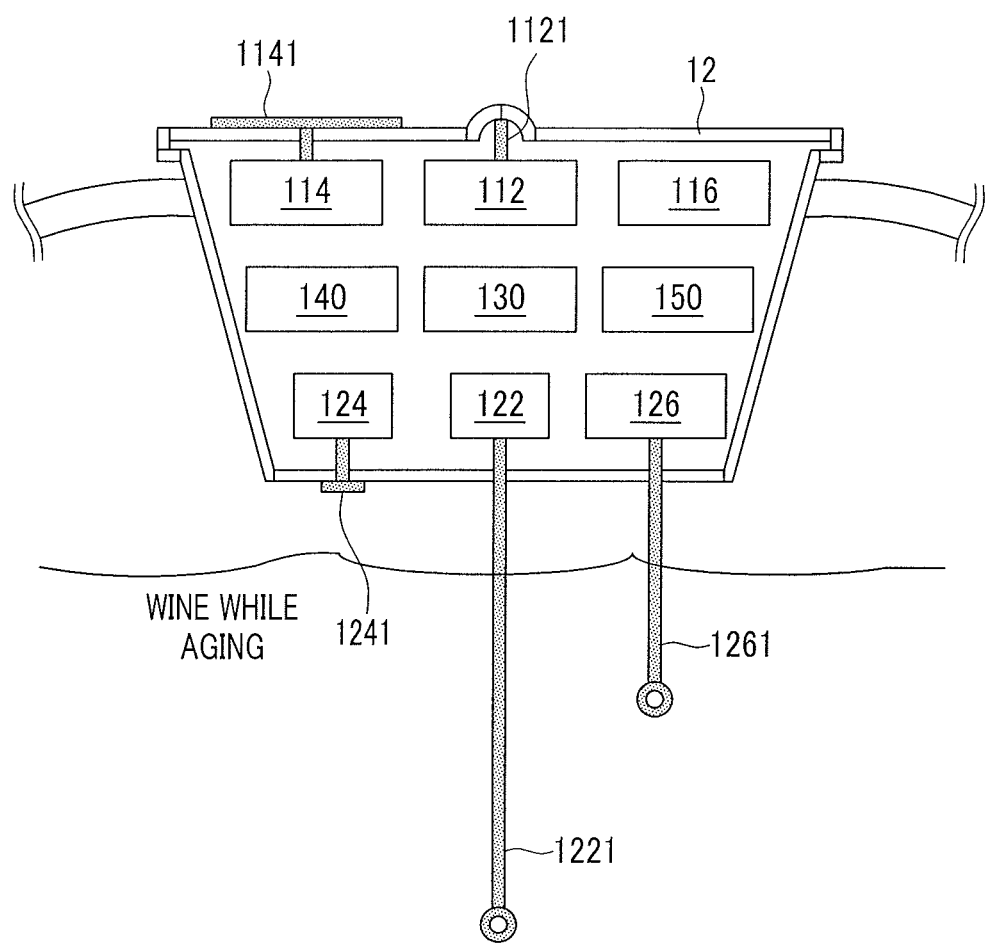
FIG. 5 is a diagram illustrating a cross-section of a bung in which an aging environment measurement apparatus is installed.

FIG. 4 is a block diagram illustrating a configuration of an aging environment measurement apparatus according to an exemplary embodiment of the present invention, and FIG. 5 is a diagram illustrating a cross-section of a bung in which an aging environment measurement apparatus is installed.

Referring to FIG. 4, the aging environment measurement apparatus 100 includes a start detection unit 110, a measurement sensing unit 120, a controller 130, a battery 140, and a wireless communication unit 150.

The start detection unit 110 detects an aging environment measurement start of the oak barrel 1, generates a start signal that orders to start aging environment measurement of the oak barrel 1, and transfers the start signal to the controller 130.

The start detection unit 110 includes a push switch 112. Further, the start detection unit 110 includes a touch sensor 114 and/or a vibration sensor 116.

The push switch 112 detects pressing of the bung 10 from the outside, and when pressing of the bung 10 is detected, the push switch 112 generates a start signal and transfers the start signal to the controller 130. Because such a push switch 112 does not consume standby power, the push switch 112 can generate a start signal with the lowest power.

When a winery manager opens the bung 10 of the oak barrel 1 for checking by the naked eye, the push switch 112 is disposed to be naturally pressed down. Thereby, during a winery management operation, aging environment data may be naturally measured.

The touch sensor 114 detects a touch of a human body, and when a touch of a human body is detected, the touch sensor 114 generates a start signal and transfers the start signal to the controller 130.

The vibration sensor 116 detects a vibration of the bung 10, and when a vibration of the bung 10 is detected, the vibration sensor 116 generates a start signal and transfers the start signal to the controller 130. A winery aging process includes a process of mixing contents as a winery manager rotates a barrel several times at a predetermined cycle, and in this case, the bung 10 may vibrate, and when the winery manager opens the bung 10, a vibration may occur. When operation of opening a barrel bung or operation of rotating a barrel is performed, the vibration sensor 116 detects a vibration of the bung 10 and generates a start signal.

The touch sensor 114 or the vibration sensor 116 receives supply of power at a predetermined cycle from the controller 130 and operates, unlike the push switch 112. The push switch 112 does not consume power, but the touch sensor 114 or the vibration sensor 116 consumes power. In order to reduce power consumption, the touch sensor 114 or the vibration sensor 116 may be used as a non-powered sensor.

As shown in FIG. 5, in order to detect an aging environment measurement start of the oak barrel 1, the push switch 112, the touch sensor 114, and/or the vibration sensor 116 of the start detection unit 110 are disposed at an upper end portion of the bung 10.

The bung 10 of the oak barrel 1 has an empty internal space and forms an outer edge frame 12 to enclose the empty space with a soft and elastic material such as silicon or rubber.

The push switch 112 is an element that detects pressing of the bung from the outside, and a push portion 1121 may protrude to the outside of the outer edge frame 12 of the bung 10 or may be positioned at the inside of the outer edge frame 12. When the push portion 1121 of the push switch 112 is positioned at the inside, a waterproof case for the aging environment measurement apparatus 100 can be more easily manufactured.

The touch sensor 114 is an element that detects a human body touch of the bung 10, a touch portion 1141 is positioned at the outside of the outer edge frame 12 of the bung 10, and the touch portion 1141 of the touch sensor 114 can be positioned in a wide area of the outside of the outer edge frame 12 of the bung 10.

The vibration sensor 116 is an element that detects a vibration of the bung 10 and is positioned within the outer edge frame 12 of the bung 10.

Referring again to FIG. 4, the measurement sensing unit 120 receives supply of power according to the control of the controller 130 and performs a measurement operation.

The measurement sensing unit 120 includes a temperature sensor 122, a carbon dioxide sensor 124, and other sensors 126. The other sensors 126 include at least one sensor that can measure pH, TA, and VA according to a kind of aging liquor.

The temperature sensor 122 measures an internal temperature of the oak barrel 1 and transfers the internal temperature to the controller 130, and the carbon dioxide sensor 124 measures an internal gas situation of the oak barrel 1 and transfers the internal gas situation to the controller 130. The other sensors 126 measure corresponding data according to a kind of each sensor and transfers the corresponding data to the controller 130.

As shown in FIG. 5, in order to measure an aging environment of the oak barrel 1, the temperature sensor 122, the carbon dioxide sensor 124, and the other sensors 126 of the measurement sensing unit 120 are disposed at a lower end portion of the bung 10.

The temperature sensor 122, the carbon dioxide sensor 124, and the other sensors 126 of the measurement sensing unit 120 include probes 1221, 1241, and 1261, respectively, and the probes 1221, 1241, and 1261 may be sunk into the wine being aged or exposed at the inside of the oak barrel 1. Because the probe 1221 of the temperature sensor 122 should measure the temperature of wine while aging, the probe 1221 of the temperature sensor 122 is sunk into the wine liquid while aging. In the temperature sensor 122, because it is useful in grasping an aging state of wine by measuring at a central portion of the oak barrel 1, the temperature sensor 122 measures a temperature around a barrel center through a long probe. When the other sensors 126 are a pH sensor, a TA sensor, and a VA sensor, probes of the sensors are sunk into the wine while aging. Because a probe of the carbon dioxide sensor 124 measures an internal gas situation of the oak barrel 1, thereof the probe 1241 is positioned at a surface of the internal bung 10 of the oak barrel 1.

Referring to FIGS. 4 and 5, when the controller 130 receives a start signal from at least one of the push switch 112, the touch sensor 114, and/or the vibration sensor 116 of the start detection unit 110, the controller 130 controls a connection of the battery 140 in order to supply power to the temperature sensor 122, the carbon dioxide sensor 124, and the other sensors 126 of the measurement sensing unit 120. Further, when the touch sensor 114 or the vibration sensor 116 of the start detection unit 110 receives supply of power and operates, the controller 130 controls a connection of the battery 140 in order to supply power to the touch sensor 114 or the vibration sensor 116.

The controller 130 receives aging environment measurement data from the temperature sensor 122, the carbon dioxide sensor 124, and the other sensors 126 of the measurement sensing unit 120, and transfers the aging environment measurement data to the gateway 200 through the wireless communication unit 150.

The battery 140 supplies power to the measurement sensing unit 120 according to the control of the controller 130. When the touch sensor 114 or the vibration sensor 116 of the start detection unit 110 receives supply of power and operates, the battery 140 supplies power to the touch sensor 114 or the vibration sensor 116 of the start detection unit 110 according to the control of the controller 130.

The wireless communication unit 150 transfers aging environment measurement data to the gateway 200 through wireless communication according to the control of the controller 130.

When transmission of aging environment measurement data to the gateway 200 is complete through the wireless communication unit 150, the controller 130 controls all elements of the aging environment measurement apparatus 100 to convert a mode thereof to a sleep mode. In this case, the controller 130 intercepts power from being supplied from the battery 140 to the measurement sensing unit 120.

When the touch sensor 114 or the vibration sensor 116 of the start detection unit 110 is formed with a non-powered sensor, the touch sensor 114 or the vibration sensor 116 continues to maintain a sleep mode. When the touch sensor 114 or the vibration sensor 116 of the start detection unit 110 receives supply of power and operates, the controller 130 sets a time to resume start detection by a timer and enters a sleep mode. Thereafter, when a timer has expired, the controller 130 awakes and supplies power to the touch sensor 114 or the vibration sensor 116, and when the touch sensor 114 or the vibration sensor 116 receives supply of power, the touch sensor 114 or the vibration sensor 116 awakes from the sleep mode and detects an aging environment measurement start.

Aging environment data on an oak barrel basis that is collected by each sensor of the measurement sensing unit 120 are collected at the gateway 200 through a sensor network that is formed by wireless, and information that is collected at the gateway 200 is transferred again to the server 300 that generalizes an entire winery.

A winery manager can grasp an aging degree of wine in an oak barrel unit in detail through aging environment data that is collected at the server 300.

Figure 6:
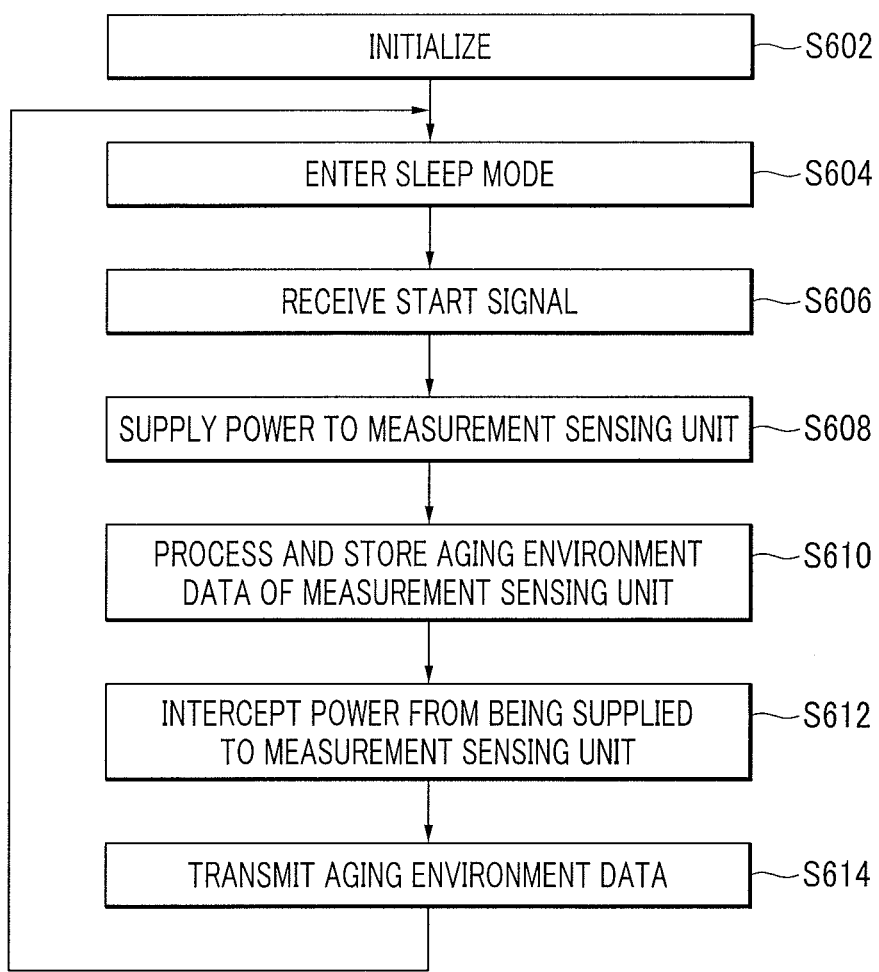
FIGS. 6 to 8 are flowcharts illustrating a method of measuring aging environment data according to the first to the third exemplary embodiments, respectively, of the present invention.

FIG. 6 is a flowchart illustrating a method of measuring aging environment data according to a first exemplary embodiment of the present invention, and illustrates a case in which the touch sensor 114 or the vibration sensor 116 of the start detection unit 110 is formed with a non-powered sensor.

When the touch sensor 114 or the vibration sensor 116 of the start detection unit 110 is formed with a non-powered sensor, the start detection unit 110 can operate without supply of power.

The measurement sensing unit 120 including the controller 130 continues to maintain a sleep mode before receiving a start signal, and when the measurement sensing unit 120 receives a start signal from the start detection unit 110, the measurement sensing unit 120 awakes from the sleep mode and starts an aging environment measurement operation.

Referring to FIG. 6, the controller 130 initializes the aging environment measurement apparatus 100 according to an initialization command from the outside (S602) and prepares aging environment measurement. Thereafter, until a start signal comes, all elements of the aging environment measurement apparatus 100 enter a sleep mode and minimize power consumption (S604).

Until the start detection unit 110 detects an aging environment measurement start of the oak barrel 1, the start detection unit 110 stands by.

When the push switch 112, the touch sensor 114, and the vibration sensor 116 of the start detection unit 110 detect the start of aging environment measurement of the oak barrel 1, the push switch 112, the touch sensor 114, and the vibration sensor 116 generate a start signal and transfer the start signal to the controller 130.

When the controller 130 receives the start signal from at least one of the push switch 112, the touch sensor 114, and the vibration sensor 116 of the start detection unit 110 (S606), the controller 130 supplies power to all sensors 122, 124, and 126 of the measurement sensing unit 120 (S608), and until each of the sensors 122, 124, and 126 of the measurement sensing unit 120 is intrinsically initialized and measured aging environment data thereof is stabilized, the controller 130 stands by.

Each of the sensors 122, 124, and 126 of the measurement sensing unit 120 measures aging environment data and transfers the measured aging environment data to the controller 130.

When the controller 130 receives aging environment measurement data of each of the sensors 122, 124, and 126 of the measurement sensing unit 120, the controller 130 processes the aging environment data and stores the aging environment data at a memory (S610). When each of the sensors 122, 124, and 126 of the measurement sensing unit 120 is an analog sensor, the controller 130 converts aging environment data of each of the sensors 122, 124, and 126 to a digital signal through analog-digital conversion (ADC) and stores the aging environment data at the memory. When each of the sensors 122, 124, and 126 of the measurement sensing unit 120 is a digital sensor, the controller 130 directly stores aging environment data of each of the sensors 122, 124, and 126 at the memory.

After storing aging environment data that is measured by each of the sensors 122, 124, and 126 of the measurement sensing unit 120 at the memory, the controller 130 intercepts power from being supplied to each of the sensors 122, 124, and 126, thereby reducing power consumption (S612).

In this case, the controller 130 repeats steps S608-S612 with the respective sensors 122, 124, and 126 of the measurement sensing unit 120 and may sequentially perform steps S608-S612 on a sensor basis, or may simultaneously apply power to all sensors 122, 124, and 126 of the measurement sensing unit 120, perform steps S610-S612 in order of a sensor having a short initialization and stabilization standby time among the sensors 122, 124, and 126, and perform step S614, in order to reduce power consumption of the aging environment measurement apparatus 100.

When aging environment data that is measured by each of the sensors 122, 124, and 126 is collected, the controller 130 transmits the aging environment data to the gateway 200 through the wireless communication unit 150 (S614).

When step S614 is terminated, the process returns again to step 604, and the controller 130 and the measurement sensing unit 120 enter a sleep mode.

Figure 7:
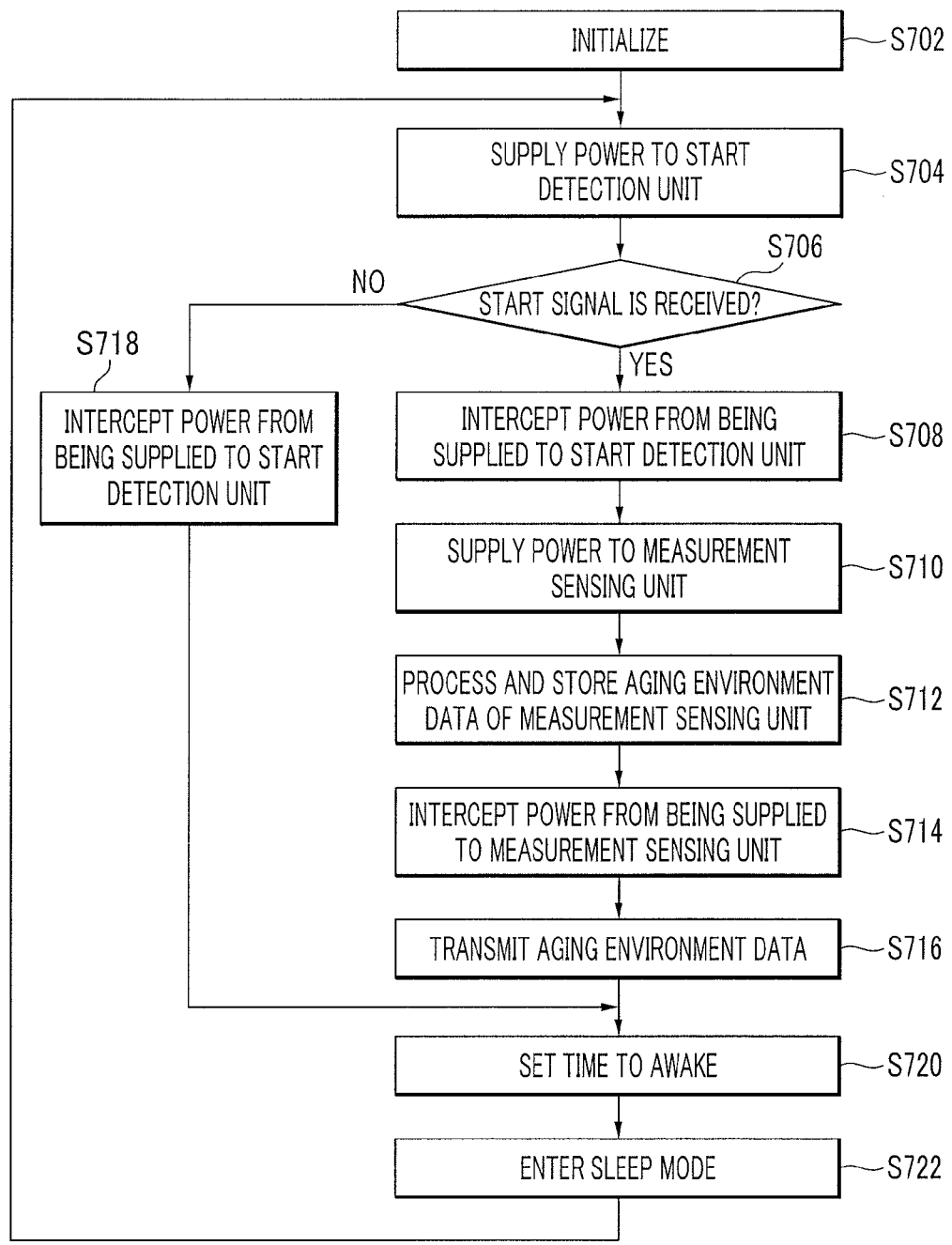

FIG. 7 is a flowchart illustrating a method of measuring aging environment data according to a second exemplary embodiment of the present invention, and illustrates a case in which the touch sensor 114 or the vibration sensor 116 of the start detection unit 110 receives supply of power and operates.

When the touch sensor 114 or the vibration sensor 116 of the start detection unit 110 receives supply of power and operates, the controller 130 should periodically supply power to the start detection unit 110, unlike the first exemplary embodiment that is shown in FIG. 6. In this case, when a cycle that supplies power to the start detection unit 110 is extended, performance of the start detection unit 110 may deteriorate and thus power should be supplied often. For example, when a winery manager starts aging environment measurement through the touch sensor 114, if the winery manager wants a measurement start with a touch within 2 seconds, a power supply cycle of the start detection unit 110 should be repeated for a time period within 2 seconds.

Referring to FIG. 7, the controller 130 initializes the aging environment measurement apparatus 100 according to an initialization command from the outside (S702) and prepares aging environment measurement.

Next, the controller 130 supplies power to the touch sensor 114 and the vibration sensor 116 of the start detection unit 110 (S704).

The touch sensor 114, the vibration sensor 116, having received the supply of power from the controller 130, and the push switch 112, start an aging environment measurement start detection of the oak barrel 1.

When the push switch 112, the touch sensor 114, and the vibration sensor 116 of the start detection unit 110 detect an aging environment measurement start of the oak barrel 1, the push switch 112, the touch sensor 114, and the vibration sensor 116 generate a start signal and transfer the start signal to the controller 130.

The controller 130 determines whether a start signal is received from the start detection unit 110 for a predetermined period (S706). If a start signal is received from the start detection unit 110 for a predetermined period, the controller 130 intercepts power from being supplied to the touch sensor 114 and the vibration sensor 116 of the start detection unit 110 (S708), and performs steps with the same method as in the first exemplary embodiment (S710-S716).

If a start signal is not received from the start detection unit 110 for a predetermined period, the controller 130 intercepts power supply to the touch sensor 114 and the vibration sensor 116 of the start detection unit 110 (S718), sets a time to awake in a next order, and enters a sleep mode (S720-S722).

When step S716 is terminated, the controller 130 sets a time to awake again in a next order (S720), unlike the first exemplary embodiment, and enters a sleep mode (S722). As described in the foregoing description, when a start detection of the touch sensor 114 is set to a time period within 2 seconds, a time to awake again may be set to a time period within 2 seconds.

When a predetermined time at step S722 has elapsed, the process returns again to step S704, and the controller 130 performs steps S704-S722.

Figure 8:
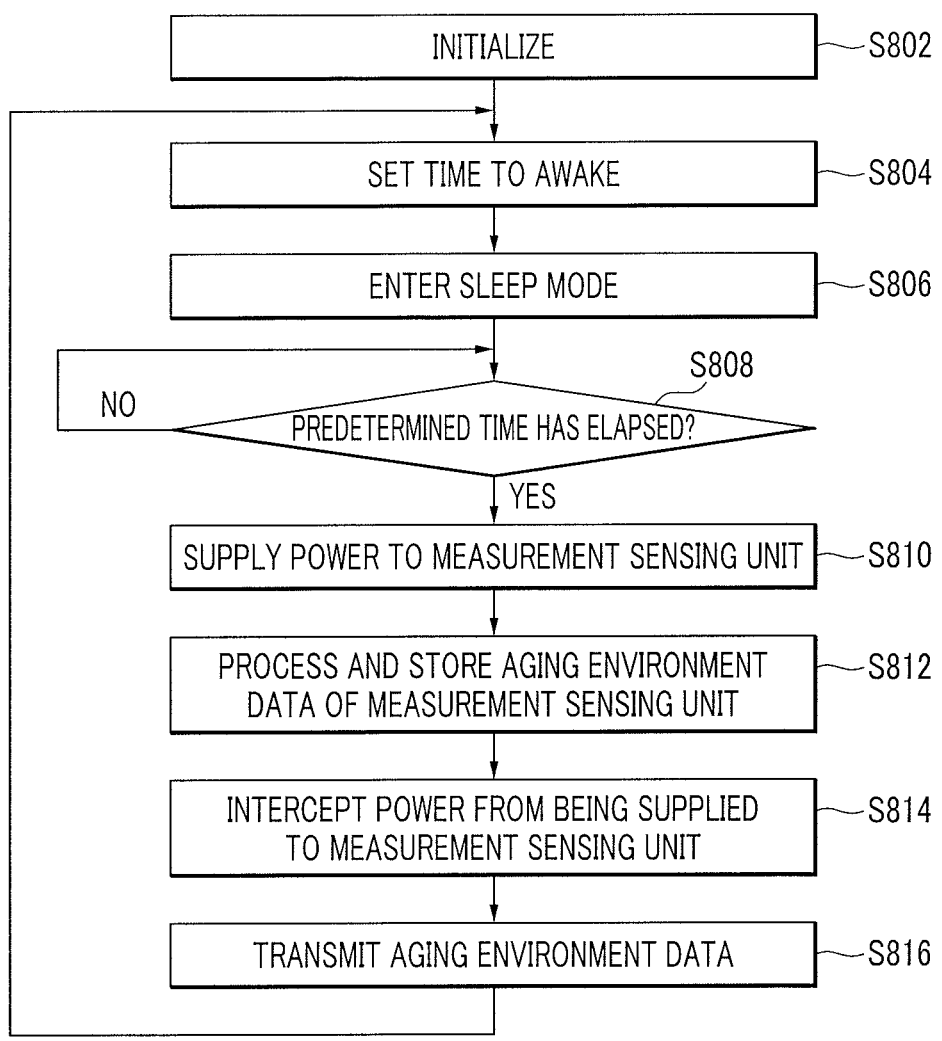

FIG. 8 is a flowchart illustrating a method of measuring aging environment data according to a third exemplary embodiment of the present invention, and illustrates periodic aging environment data measurement by time setting, unlike a case of FIGS. 6 and 7.

Periodic aging environment measurement by time setting corresponds to a case of repeatedly measuring aging environment data according to a preset cycle and does not require a start signal of the start detection unit 110. However, periodic aging environment measurement by time setting may be simultaneously performed with a method that is described in FIGS. 6 and 7.

In periodic aging environment measurement by time setting, the aging environment measurement apparatus 100 should periodically awake and repeat an aging environment measurement operation. In general, because an aging environment measurement cycle is a minimum minute unit or more and may be measured in a day unit, a frequency in which the aging environment measurement apparatus 100 awakes may be much smaller than that of the second exemplary embodiment. Therefore, power consumption of the aging environment measurement apparatus 100 may be smaller than that of the second exemplary embodiment, and may be similar to that of the first exemplary embodiment.

Referring to FIG. 8, the controller 130 initializes the aging environment measurement apparatus 100 according to an initialization command from the outside (S802), and prepares aging environment measurement.

The controller 130 sets a time to awake in a next order according to an aging environment measurement cycle (S804) and enters a sleep mode (S806).

When a predetermined time that is set at step (S804) has elapsed (S808), the controller 130 awakes. Then the controller 130 collects aging environment data with the same method as that of the first exemplary embodiment and transmits the aging environment data to the gateway 200 (S810-S816).

When step (S816) is terminated, the process returns again to step (S804), and the controller 130 sets a time to awake in a next order and enters a sleep mode.

According to an exemplary embodiment of the present invention, by attaching a sensor to a barrel bung that can be recycled and be movably attached to an oak barrel, an actual aging state of wine while aging within the barrel can be accurately measured with a low cost in a winery.

Further, in a process in which wine manufacturers periodically open and check the barrel bung by the naked eye, by detecting pressing of the bung with a push switch or a touch sensor, an aging environment can be measured, and even in a normal operation in which wine manufacturers periodically rotate the barrel and mix contents, by detecting this through a vibration sensor, an aging environment can be measured. Therefore, the wine manufacturer can automatically measure an aging environment at a desired time point without any additional procedure.

Further, because an aging environment measurement apparatus can be applied to a brewery in which a barrel is used, the aging environment measurement apparatus can be applied to various brewing environments such as for beer or whisky production as well as wine production.

An exemplary embodiment of the present invention may be not only embodied through the above-described apparatus and/or method, but may also be embodied through a program that executes a function corresponding to a configuration of the exemplary embodiment of the present invention or through a recording medium on which the program is recorded, and can be easily embodied by a person of ordinary skill in the art from a description of the foregoing exemplary embodiment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An aging environment measurement apparatus that measures an aging environment within an oak barrel that contains liquor, the aging environment measurement apparatus comprising:
   a measurement sensing unit that measures aging environment data within the oak barrel;
   a controller that collects the aging environment data and transmits the collected aging environment data to a server, wherein the aging environment measurement apparatus is mounted in a bung of the oak barrel,
   a start detection unit that generates a start signal according to detection of an aging environment measurement start, wherein the controller supplies power to the measurement sensing unit according to the start signal, wherein the start detection unit comprises at least one of:
a push switch that detects pressing of the bung from the outside and that generates the start signal;
a touch sensor that senses touch of the bung from the outside and that generates the start signal; and
a vibration sensor that senses a vibration of the bung and that generates the start signal.

2. The aging environment measurement apparatus of claim 1, wherein the controller enters a sleep mode when transmission of the aging environment data is complete, and awakes from the sleep mode according to the start signal.

3. The aging environment measurement apparatus of claim 2, wherein the controller intercepts power from being supplied to the measurement sensing unit before entering the sleep mode.

4. The aging environment measurement apparatus of claim 1, wherein the touch sensor and the vibration sensor are non-powered sensors.

5. The aging environment measurement apparatus of claim 1, wherein the measurement sensing unit comprises:
a temperature sensor that measures a temperature of liquor liquid; and
a carbon dioxide sensor that measures a gas situation within the oak barrel.

6. The aging environment measurement apparatus of claim 1, wherein the controller supplies power to the measurement sensing unit according to an aging environment measurement cycle.

7. The aging environment measurement apparatus of claim 6, wherein the controller enters a sleep mode when transmission of the aging environment data is complete, and awakes from the sleep mode according to the aging environment measurement cycle.

8. The aging environment measurement apparatus of claim 7, wherein the controller intercepts power from being supplied to the measurement sensing unit before entering the sleep mode.

9. The aging environment measurement apparatus of claim 1, wherein the bung comprises an outer edge frame that encloses to form an empty space, and
the aging environment measurement apparatus is mounted in the empty space.

10. The aging environment measurement apparatus of claim 1, wherein the aging environment data comprises at least one of temperature, pH, tartaric acid, volatile acidity, and carbon dioxide.

11. A method in which an aging environment measurement apparatus measures an aging environment within an oak barrel that contains liquor, the method comprising:
measuring aging environment data within the oak barrel, wherein the aging environment measurement apparatus is mounted in a bung of the oak barrel and wherein the measuring of aging environment data comprises:
detecting an aging environment measurement start, wherein detecting of an aging environment measurement start comprises at least one of:
detecting a vibration of the bung;
detecting a human body touch of the bung; and
detecting pressing of the bung;
supplying power to a measurement sensing unit that measures the aging environment data according to detection of the aging environment measurement start; and
transmitting the aging environment data within the oak barrel to a server, wherein transmitting of the aging environment data comprises:
processing and storing the aging environment data; and
intercepting power from being supplied to the measurement sensing unit when processing and storage of the aging environment data are complete.

12. The method of claim 11, wherein the transmitting of the aging environment data comprises entering a sleep mode when processing and storage of the aging environment data are complete.

13. The method of claim 11, wherein the measuring of aging environment data comprises supplying power to the measurement sensing unit that measures the aging environment data according to an aging environment measurement cycle,
wherein the transmitting of the aging environment data comprises:
processing and storing the aging environment data; and
intercepting power from being supplied to the measurement sensing unit when processing and storage of the aging environment data are complete.

14. The method of claim 13, wherein the transmitting of the aging environment data comprises intercepting the power supply and setting a time to awake, and entering a sleep mode according to the aging environment measurement cycle.

* * * * *